United States Patent [19]

Kadota et al.

[11] Patent Number: 5,207,986
[45] Date of Patent: May 4, 1993

[54] AUTOMATIC ANALYZER

[75] Inventors: Toshimi Kadota; Koji Tanimizu, both of Kyoto, Japan

[73] Assignee: Shimadzu Corporation, Kyoto, Japan

[21] Appl. No.: 675,179

[22] Filed: Mar. 26, 1991

[30] Foreign Application Priority Data

Mar. 30, 1990 [JP] Japan ................... 2-87233
Apr. 27, 1990 [JP] Japan ................... 2-113829

[51] Int. Cl.⁵ .............................................. G01N 33/50
[52] U.S. Cl. ........................................ 422/65; 436/48;
436/47; 198/468.3; 198/468.11; 198/473.1;
198/747
[58] Field of Search ............... 422/63, 65, 64, 67;
198/468.3, 468.11, 469.1, 473.1, 583, 747;
436/47, 48

[56] References Cited

U.S. PATENT DOCUMENTS

| Re. 30,627 | 5/1981 | Bagshawe et al. | 422/63 |
|---|---|---|---|
| 3,272,240 | 9/1966 | Roth | 198/747 |
| 3,302,772 | 2/1967 | Alsop | 198/747 |
| 4,046,248 | 9/1977 | Goffredo et al. | 198/583 |
| 5,008,082 | 4/1991 | Shaw | 422/65 |

FOREIGN PATENT DOCUMENTS 60-188849 9/1985 Japan .................... 422/65

*Primary Examiner*—Lynn M. Kummert
*Attorney, Agent, or Firm*—William L. Klima

[57] ABSTRACT

A rack supply part, an analysis unit part and a rack storage part are formed as units which are separable from each other, and a rack carrier part is integrally mounted on the analysis unit part. The respective units are provided with locating members for coupling the units in a direction for transferring a sample rack.

Since the rack carrier part is integrated with the analysis unit part, relative positional relation between a position for stopping the sample rack and a position for stopping a sample dispensing pipetter provided in the analysis unit part for attraction is not displaced even if the units are separated from each other and then recombined with and mounted on each other. Thus, location is easy and no fine adjustment of positional relation is required.

20 Claims, 4 Drawing Sheets

PRIOR ART

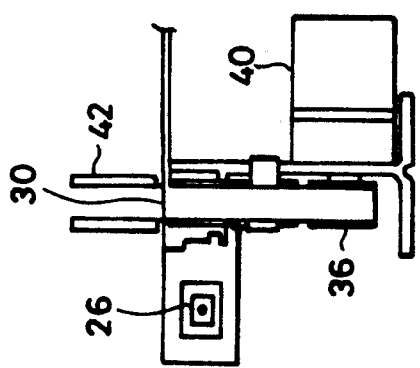
FIG.2C
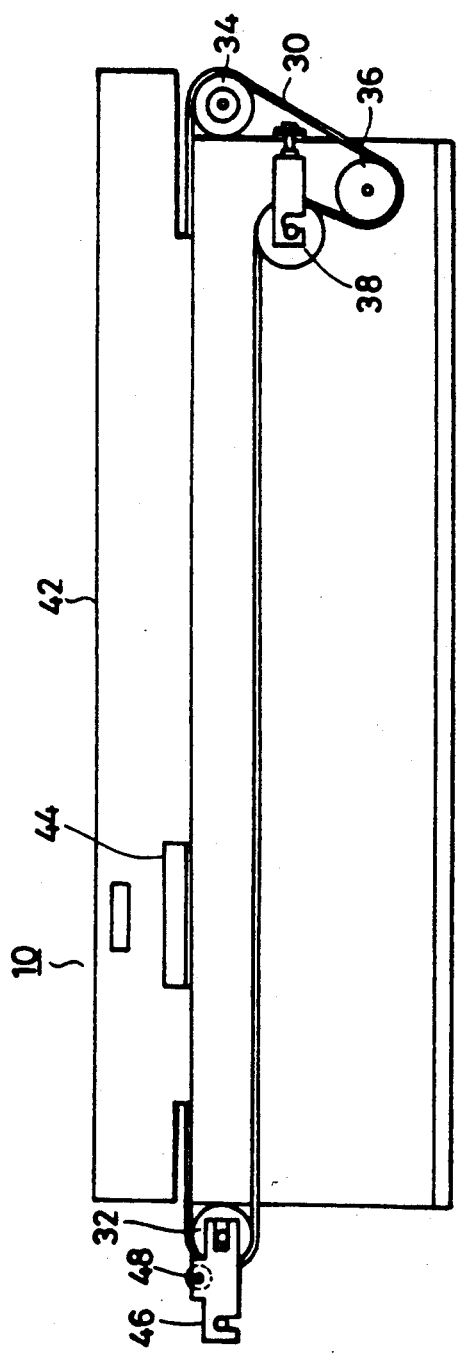
FIG.2A
FIG.2B
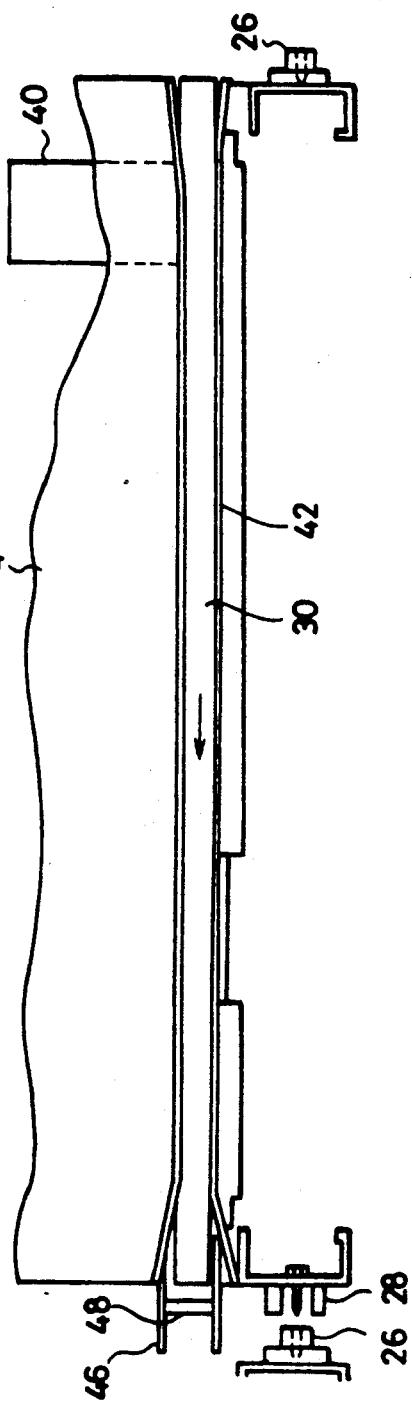

AUTOMATIC ANALYZER

BACKGROUND OF THE INVENTION

1. Field of the Invention

The present invention relates to an automatic analyzer, in which an analysis unit part is arranged along a rack carrier part for carrying sample racks each arranging and holding a plurality of sample containers.

The inventive automatic analyzer is suitably applied to biochemical analysis of blood or urine, for example, or immunity analysis, etc.

2. Description of the Background Art

In the field of clinical biochemical analysis, automation has promoted since quick analytical results are required as to a number of samples, and various systems of automatic biochemical analyzers are now being used.

As one of such automatic biochemical analyzers, well known is an analyzer in a system of employing a plurality of rectangular sample racks, which can arrange constant numbers of samples in prescribed order and hold the same, distributing large numbers of samples on the sample racks and successively transferring the same to dispensing positions of analysis parts through a belt conveyor type sample rack transfer path.

FIG. 7 is an exploded view illustrating an exemplary automatic analyzer, in which sample racks holding samples are transferred from a rack supply part to a rack storage part while analysis unit parts are arranged along a rack carrier part provided therebetween.

A rack carrier part 102 carries sample racks 104 with a belt, and a rack supply part 106 is provided on an inlet side along a rack transfer direction of the rack carrier part 102, while a rack storage part 108 is provided on an outlet side. A pair of analysis unit parts 110 and 112 are arranged along the rack carrier part 102. Each of the analysis unit parts 110 and 112 is provided with a reaction line comprising a plurality of reaction tubes, a reagent supply part for supplying a reagent to the reaction tube, a measuring part for detecting reaction, and the like. Numerals 114 and 116 denote pipetters for dispensing the samples, which have been transferred by the rack carrier part 102, to the reaction tubes provided in the analysis unit parts 110 and 112 respectively.

Referring to FIG. 7, the rack supply part 106, the rack carrier part 102 and the rack storage part 108 are integrally coupled with each other, and the analysis unit parts 110 and 112 are horizontally movable so that the same can be frontwardly separated from the rack carrier part 102 for maintenance. In order to re-mount the analysis unit parts 110 and 112, which have been thus separated from the rack carrier part 102, locating pins 118 and 120 are provided between the rack carrier part 102 and the analysis unit parts 110 and 112.

When the analysis unit parts 110 and 112 are mounted on the rack carrier part 102, extremely important is relative positional relation between stop positions of the racks for attracting the samples and those of the pipetters 114 and 116 for such attraction. Such importance of the positional relation between the stop positions of the racks and the pipetters 114 and 116 for attraction of the samples is increased as the samples are refined and samples cups or blood collection tubes are reduced in size. Therefore, precision is required for the locating pins 118 and 120 and the cost is increased, while complicated position control is required after mounting.

SUMMARY OF THE INVENTION

An object of the present invention is to eliminate necessity for a precise mechanism for location in mounting after separation and for a location checking step in an automatic analyzer in which some parts are brought into separable states for convenience of maintenance.

According to the present invention, analysis unit parts are structured as units which are separable from a rack supply part and a rack storage part, while a rack carrier part is integrally mounted on the analysis unit parts.

The automatic analyzer according to the present invention comprises:

at least one analysis unit integrally comprising a rack carrier part of a belt conveyor system for transferring sample racks arranging and holding a plurality of sample containers, which is unified with functions required for collecting samples from the sample racks transferred by the rack carrier part and analyzing the same, and including locating members to be combined with those of other units in a sample rack transfer direction of the rack carrier part;

a rack supply part which is structured as a unit separable from the analysis unit part, comprising a locating member to be combined with one of the locating members of the analysis unit part, containing a plurality of such sample racks and including sample rack guide means for successively feeding the sample racks to the rack carrier part of the analysis unit part by the sample rack guide means; and a rack storage part which is structured as a unit separable from the analysis unit part, comprising a locating member to be combined with the other one of the locating members of the analysis unit part, and receiving and storing the sample racks after completion of measurement.

An automatic analyzer according to another aspect of the present invention comprises:

at least one analysis unit part integrally comprising a rack carrier part of a belt conveyor system having an approach carrier path and a return carrier path for transferring sample racks arranging and holding a plurality of sample containers in opposite directions, which is unified with functions required for collecting samples from the sample rack transferred by the rack carrier part and analyzing the same, and including locating members to be combined with those of other units in sample rack transfer directions of the rack carrier part;

a rack supply and storage part which is coupled to an end of the analysis unit part or a combination formed by continuously coupling at least two such analysis unit parts, structured as a unit separable from the analysis unit part, comprising a locating member to be combined with one of the locating members of the analysis unit part, storing a plurality of such sample racks, including sample rack guide means for successively feeding the sample racks to the rack carrier part of the analysis unit part by the sample rack guide means, and receiving and storing the sample racks after completion of measurement; and a return part which is coupled to the other end of the analysis unit part or the combination formed by continuously coupling at least two such analysis unit parts, structured as a unit separable from the analysis unit part, comprising a locating member to be combined with the other one of the locating members of the analysis unit part, and returning the sample racks transferred through the approach carrier path of the rack carrier part to the return carrier path of the rack carrier part.

The most important locational accuracy is required for the relative positional relation between a position for stopping the sample racks and a position for stopping a pipetter, which is provided in the analysis unit part, for attraction. Since the rack carrier part is integrally and inseparably mounted on the analysis unit part, the relative positional relation between the position for stopping the sample racks and that for stopping the pipetter for attraction is not displaced even if the units are separated from each other and again combined with and mounted on each other, so far as the said positional relation is adjusted in the initial stage of assembling. Thus, location is easy and no fine adjustment of positional relation is required, whereby the analyzer can be structured at a low cost.

Since the rack carrier part is integrally mounted on the analysis unit part, it is easy to increase the number of such analysis unit parts.

On the other hand, it is necessary to carry out location with respect to a sample rack progress direction in the rack carrier parts for re-assembling the units after separation, since the rack carrier part is integrally mounted on the analysis unit part. However, an allowable width of displacement with respect to the sample rack progress direction is extremely large as compared with that of displacement for the position for stopping the pipetter for attraction, such that no problem is caused even if a carrier belt is displaced by about 5 mm in the vertical direction or by about 3 to 4 mm in the cross direction, in more concrete terms. On the other hand, an allowable range for displacement of the position for stopping the pipetter for attraction is merely about 1 mm.

These and other objects, features, aspects and advantages of the present invention will become more apparent from the following detailed description of the present invention when taken in conjunction with the accompanying drawings.

BRIEF DESCRIPTION OF THE DRAWINGS

FIG. 2A is a front elevational view showing a rack carrier part of the embodiment shown in FIG. 1, FIG. 2B is a plan view, and FIG. 2C is a right side elevational view of the rack carrier part;

DESCRIPTION OF THE PREFERRED EMBODIMENTS

Figure 1:
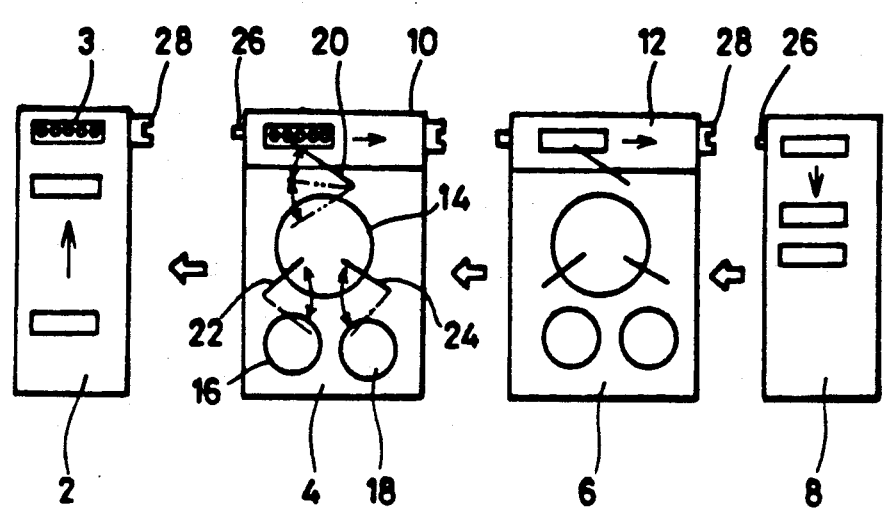
FIG. 1 is a schematic plan view showing an embodiment in a state separated into respective parts.
Figure 7:
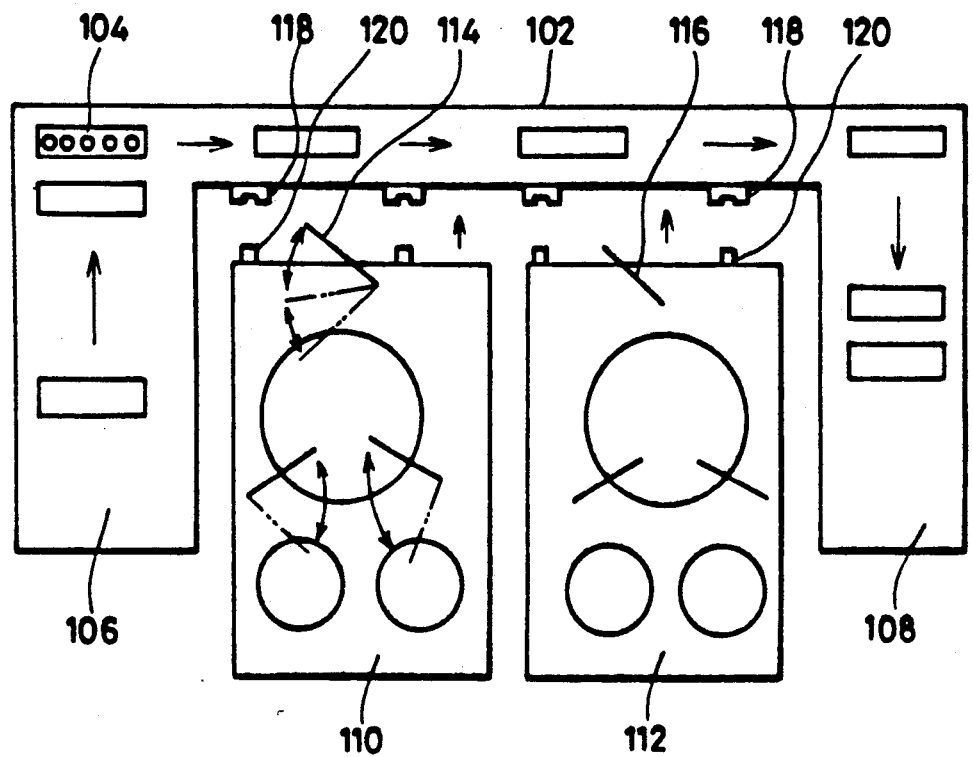
FIG. 7 is a schematic plan view showing a conventional apparatus.

FIG. 1 illustrates an embodiment of the present invention in a state separated into respective parts.

Numeral 2 denotes a rack supply part, numeral 3 denotes a sample rack on which containers for samples (including subjects, standard solutions, contrast solutions and the like) are arranged, numerals 4 and 6 denote analysis unit parts and numeral 8 denotes a rack storage part. A rack carrier part 10 is integrally mounted on the analysis unit part 4, while another rack carrier part 12 is integrally mounted on the other analysis unit part 6. The rack supply part 2, the analysis unit parts 4 and 6, and the rack storage part 8 are structured as units which are separable from each other.

The analysis unit parts 4 and 6 are identical in structure to each other. Each of the analysis unit parts 4 and 6 is provided with a reaction disk 14 on which reaction tubes are arranged along its circumference, and reagent turntables 16 and 18 on which reagents to be supplied to the reaction tubes are arranged along the circumferences thereof. Numeral 20 denotes a pipetter for dispensing the samples from a sample dispensing position of the rack carrier part 10 to the reaction tubes provided on the reaction disk 14, and numerals 22 and 24 denote reagent dispensing nozzles for supplying the reagents provided on the reagent turntables 16 and 18 to the reaction tubes provided on the reaction disk 14. Each analysis unit part is further provided with a stirrer for stirring reaction solutions which are contained in the reaction tubes provided on the reaction disk 14, a cleaning device for cleaning the reaction tubes after reaction, a spectrograph for measuring absorbance levels of the reaction solutions contained in the reaction tubes thereby measuring reaction, and the like, although such elements are not shown in the figure.

Locating pins 26 and 28 are adapted to locate the rack supply part 2, the analysis unit parts 4 and 6, and the rack storage part 8 when the same are assembled with each other. The locating pin 28 provided in the rack supply part 2 is engaged with the locating pin 26 provided in the analysis unit part 4, while other pairs of such locating pins provided in the respective parts are similarly engaged with each other, to locate the parts in mounting.

FIG. 2(A) is a front elevational view showing the rack carrier part 10, which is integrally mounted on the analysis unit part 4 in the embodiment shown in FIG. 1, FIG. 2(B) is a plan view, and FIG. 2(C) is a right side elevational view of the rack carrier part 10. While these figures show only the rack carrier part 10, the other rack carrier part 12, which is integrally mounted on the analysis unit part 6, has the same structure.

The rack carrier part 10 is provided with a belt line of a belt conveyor, in order to transfer the sample rack. A belt 30 for transferring the sample rack is extended by pulleys 32, 34, 36 and 38, and the pulley 36 is driven by a motor 40, to drive the belt 30. Guides 42 are provided in order to guide the sample rack which is transferred by the belt 30. The guides 42 are formed by a pair of plate members which are uprightly provided along the direction of progress of the sample rack, and both end portions thereof are increased in width so that the same are easily coupled with adjacent portions. The guides 42 are provided on parts thereof with openings 44, which are provided with stoppers for stopping the sample rack for dispensation.

The locating pins 26 and 28 are provided in the vicinity of both end portions of the rack carrier part 10 respectively. On the left end of FIG. 2(B), the locating pin 28 is combined with the locating pin 26 which is provided on the other analysis unit part 6, for example. The locating pin 26 is in the form of a projection, and the locating pin 28 is provided with a groove to be engaged with the locating pin 26. Further, the locating pin 26 has a screwhole, while the locating pin 28 is provided with a screw which is inserted in the screwhole of the locating pin 26 for fixing the locating pin 28 to the locating pin 26.

Coupling members 46 having rollers 48 are inserted in coupling parts between the analysis unit parts 4 and 6, between the analysis unit part 4 and the rack supply part 2 and between the analysis unit part 6 and the rack storage part 8, so that no clearances are defined therebetween when these parts are coupled with each other.

An identification mark such as a bar code is provided on the side surface of the sample rack 3 which is employed in this embodiment, so that the identification mark is read by optical read means (OCR bar code reader) when the sample rack 3 is supplied from the rack supply part 2 to the rack carrier part 10, and the read information is inputted in an analysis part for identification etc. Such optical read means is provided in an intermediate position of sample rack guide means for moving the sample rack 3 from the sample rack supply part 2 to an end of the rack carrier part 10.

Figure 3:
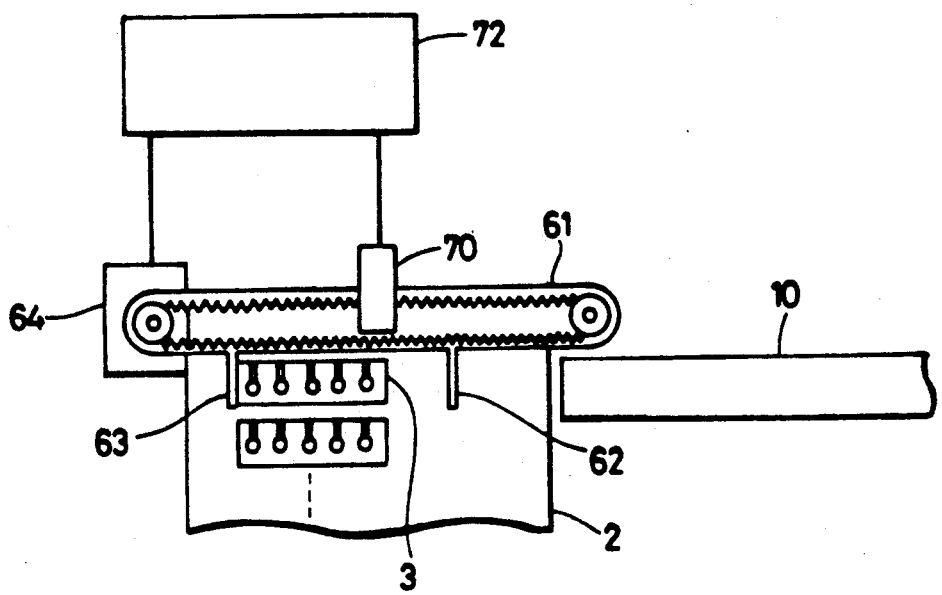
FIGS. 3 and 4 are schematic plan views for illustrating an essential part of the rack supply part provided in the embodiment and its function respectively.

As shown in FIG. 3, such sample rack guide means is formed by an endless belt 61 having projecting profiles 62 and 63 and a reversible motor 64 for rotating the endless belt 61, while the aforementioned optical read means 70 is provided substantially at the central portion of the guide means. The profiles 62 and 63 have spaces exceeding the length of the sample rack 3, and the profile 63 is adapted to move the sample rack 3 toward the rack carrier part 10 while the profile 62 is adapted to move the sample rack 3 in a direction opposite thereto. Numeral 72 denotes a control part for controlling the rack carrier parts 10 and 12 and the read means 70.

The operations of the sample rack guide means and the read means 70 are now described.

First, a transfer mechanism (not shown) arranges the sample rack 3, which has been stored in the sample rack supply part 2, on a front stage of the read means 70 in a guide region of the sample rack guide means. FIG. 3 shows this state.

Figure 4:
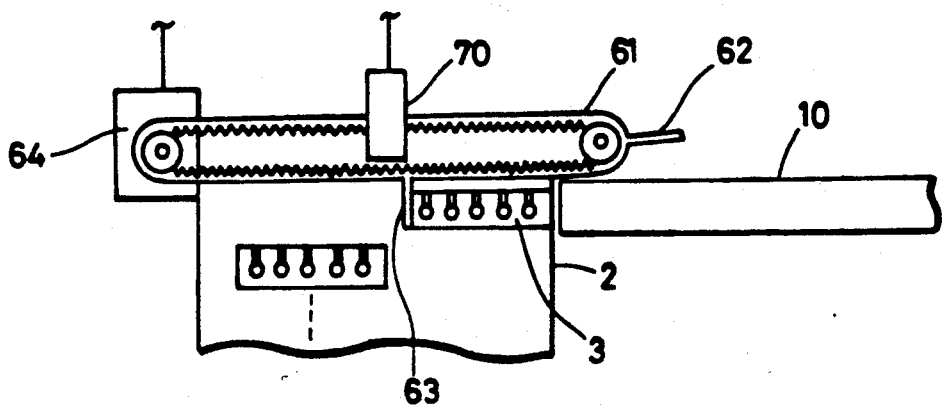

Then, the motor 64 operates to anticlockwisely rotate the belt 61 in the figure, whereby the sample rack 3 is linearly constantly moved toward the rack carrier part 10. In the process of such movement, the side surface of the sample rack 3 crosses a front read surface of the read means 70, which in turn reads the bar code. FIG. 4 shows a position of the sample rack 3 immediately after such reading. Since the profile 62 of the belt 61 is retracted from the progress direction, the belt 61 is continuously rotated when the bar code is properly read, whereby the sample rack 3 is moved to and placed on an end of the carrier part 10 which is rightwardly driven in the figure at a constant speed, and transferred to the analysis unit parts 4 and 6 to be subjected to an analysis operation.

If the reading operation is defective or impossible, on the other hand, the control part 72 clockwisely, i.e., oppositely rotates the belt 61 to return the sample rack 3 to the position shown in FIG. 3 by the profile 62, and then again anticlockwisely rotates the belt 61 to move the sample rack 3 toward the rack carrier part 10, read the bar code, transfer and place the same to and on the end of the rack carrier part 10.

According to the sample rack guide means and the read means 70, a re-reading operation is automatically made when a read error is caused by the read means 70, whereby it is possible to avoid interruption of the operation of the analyzer, re-testing of the sample rack 3 and the like, to remarkably improve efficiency of the analysis operation.

Figure 5:
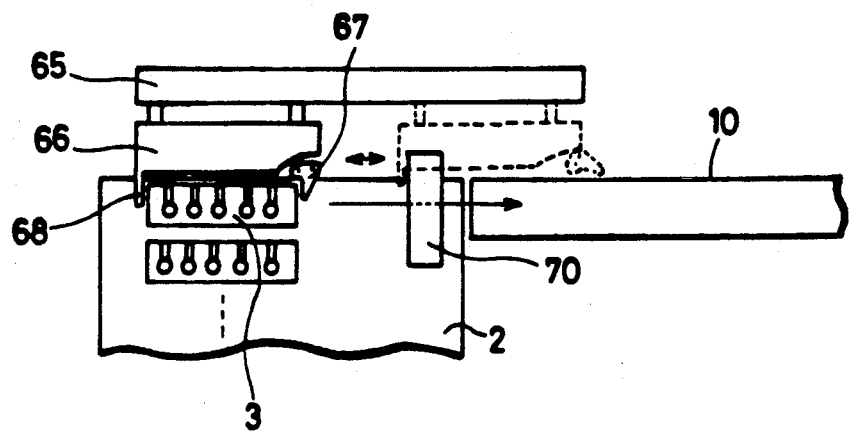
FIG. 5 is a schematic plan view showing an essential part of another example of the rack supply part.

Although the sample rack guide means is of an endless belt system in the embodiment shown in FIGS. 3 and 4, it is possible to alternatively use a reciprocatively movable sample rack holding means, which can control holding and release of a sample rack 3 by a cam 67, as shown in FIG. 5.

This sample rack holding means comprises a movable member 66 which is reciprocatively moved in a rack carrier part direction along a moving shaft 65, a projection 68 provided on the movable member 66 for pushing the rear end of the sample rack 3 and feeding the same toward the rack carrier part, and the cam 67 which is provided on the movable member 66 in a position separated from the projection 68 by a distance exceeding the length of the sample rack 3 along the progress direction of the sample rack 3, to be not engaged with the sample rack 3 when the movable member 66 is moved to feed the same toward the rack carrier part while being engaged with the sample rack 3 when the movable member 66 oppositely returns the same.

Broken lines appearing in FIG. 5 show a state of the sample holding means after a proper reading operation.

Figure 6:
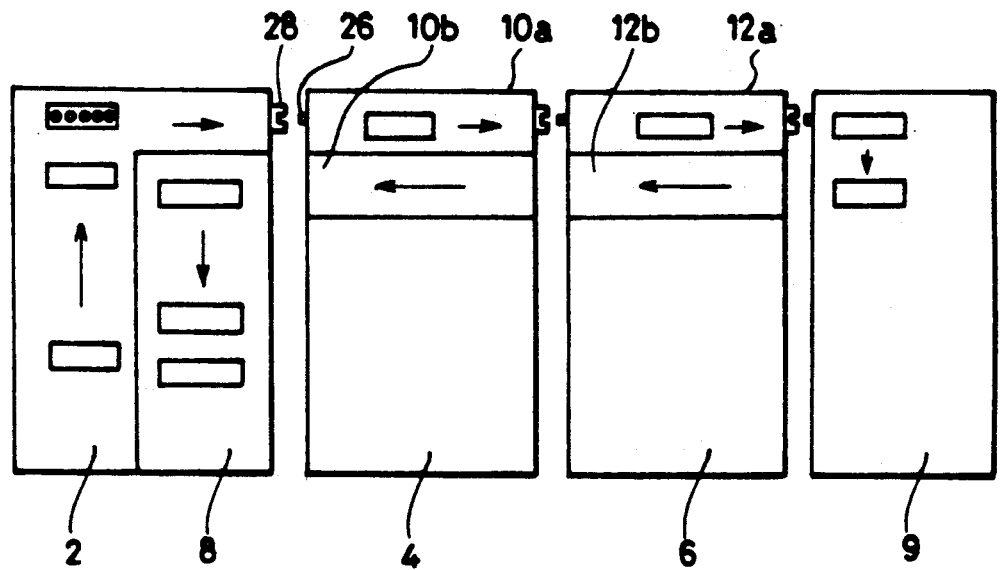
FIG. 6 is a schematic plan view showing another embodiment of the present invention in a state separated into respective parts.

FIG. 6 shows another embodiment of the present invention.

Referring to FIG. 6, both of a rack supply part 2 and a rack storage part 8 are provided on one side of the overall analyzer, while a return part 9 for returning a sample rack carried thereto is provided on an opposite side to the rack supply part 2 and the rack storage part 8 through analysis unit parts 4 and 6. A rack carrier part, which is integrally mounted on the analysis unit part 4, is formed by an approach path 10a and a return path 10b having opposite transfer directions, while another rack carrier part, which is integrally mounted on the analysis unit part 6, is also formed by an approach path 12a and a return path 12b having opposite transfer directions.

Locating pins 26 and 28 are provided for locating the respective parts.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. An automatic analyzer, comprising:
at least one analysis unit part including means for conducting a biochemical or chemical analysis, said analysis unit part integral comprising a rack carrier part of a belt conveyor system for transferring a sample rack used for arranging and holding a plurality of sample containers, means for collecting samples from said sample rack transferred by said rack carrier part and analyzing the samples, and locating members constructed and arranged to be coupled with locating members of another analysis unit part, said locating members of said analysis unit part oriented in a sample rack transfer direction of said rack carrier part;
a rack supply part structured as a unit separable from said analysis unit part, said rack supply pat comprising a locating member constructed and arranged to be coupled with a locating member of said analysis unit part, said rack supply part configured for containing a plurality of sample racks and including sample rack guide means for successively feeding sample racks to said rack carrier part of said analysis unit part; and a rack storage part structured as a unit separable from said analysis unit part, said rack storage part comprising a locating member constructed and arranged to be coupled with an opposite locating member of said analysis unit part, and configured for receiving and storing sample racks after completion of measurements of the samples.

2. An automatic analyzer in accordance with claim 1, including another analysis unit part having locating members, said analysis unit parts continuously coupled by said locating members, said rack supply part coupled to an end portion of a combination of said analyzer unit parts by said locating members while said rack storage part is coupled to an opposite end portion of said combination by said locating members.

3. An automatic analyzer in accordance with claim 1, wherein said locating members are provided in the vicinity of opposite end portions of said rack carrier part with respect to the sample rack transfer direction.

4. An automatic analyzer in accordance with claim 1, wherein one of a pair of said locating members to be combined with each other is a projection and the other one is a groove to be engaged with said projection, said projection being screwed and fixed in a state inserted in said groove.

5. An automatic analyzer in accordance with claim 1, wherein said sample racks are provided with identification marks for said samples to be measured, said sample rack guide means of said rack supply part is configured for oppositely selectively transferring sample racks during different transferring operations, and including an optical read means arranged in an intermediate position of said sampler rack guide means for reading said identification marks provided on the sample racks.

6. An automatic analyzer in accordance with claim 5, wherein said sample rack guide means comprises an endless belt with two projections spaced apart a predetermined distance having a length that is greater than the length of a sample rack, and including a reversible motor for driving said endless belt.

7. An automatic analyzer in accordance with claim 5, wherein said sample rack guide means comprises sample rack holding means that is selectively moveable in opposite directions along the direction of said rack a carrier part, and constructed and arranged for holding and releasing sample racks with a cam.

8. An automatic analyzer in accordance with claim 7, wherein said sample rack holding means comprises a moveable member that is selectively moveable in opposite directions along the direction of travel of said rack carrier part, a projection is provided in said moveable member for pushing a rear end of said sample rack and feeding the rack toward said rack carrier part, and a cam is provided in said moveable member at a position separated form said projection by a distance exceeding the length of each sample rack in a direction of travel of the sample racks, said cam is not engaged with a sample rack when said moveable member is moved in a direction for feeding said sample rack to said rack carrier part, and said cam is engaged with said sample rack when said moveable member returns said sample rack in an opposite direction.

9. An automatic analyzer, comprising:

a least one analysis unit part including means for biochemical or chemical analysis, said analysis unit part integrally comprising a rack carrier part of a belt conveyor system having an approach carrier path and a return carrier path for transferring a sample rack used for arranging and holding a plurality of sample containers in opposite directions, means for collecting samples from said sample rack transferred by said rack carrier part and analyzing the samples, and a locating member constructed and arranged to be coupled with a locating member of another analysis unit part, said locating member of said analysis unit part oriented in sample rack transfer directions of said rack carrier part;

a rack supply and storage part coupled to an end of said analysis unit part, said rack supply and storage part comprising a locating member constructed and arranged to be coupled with said locating member of said analysis unit part, said rack supply and storage part configured for storing a plurality of sample racks, said rack supply and storage part including sample rack guide means for successively feeding sample racks to said rack carrier part of said analysis unit part, and means for receiving and storing sample racks after completion of measurement; and a return part coupled to an opposite end of said analysis unit part, said return part structured as a unit separable from said analysis unit part, said return part comprising a locating member constructed and arranged to be coupled with said locating member of said analysis unit part, and means for returning sample racks transferred through said approach carrier path of said rack carrier part to said turn carrier path of said rack carrier part.

10. An automatic analyzer in accordance with claim 9, wherein said locating members are provided in the vicinity of both end portions of said rack carrier part.

11. An automatic analyzer in accordance with claim 9, wherein one of a pair of said locating members to be combined with each of the is a projection and the other one is a groove to be engaged with said projection, said projection being screwed and fixed in a state inserted in said groove.

12. An automatic analyzer in accordance with claim 9, wherein said sample racks are provided with identification marks for said samples of be measured, said sample rack guide means of said rack supply part is configured for oppositely selectively transferring sample racks during different transferring operations, and including an optical read means arranged in an intermediate position of said sample rack guide means for reading said identification marks provided on the sample racks.

13. An automatic analyzer in accordance with claim 12, wherein said sample rack guide means comprises an endless belt with two projections spaced apart a predetermined distance having a length that is greater than the length of a sample rack, and including reversible motor for ridge said endless belt.

14. An automatic analyzer in accordance with claim 12, wherein said sample rack guide means comprises sample rack holding means that is selectively moveable in opposite directions along the direction of said rack carrier part, and constructed and arranged for holding and releasing sample racks with a cam.

15. An automatic analyzer in accordance with claim 14, wherein said sample rack holding means comprises a moveable member that is selectively moveable in opposite directions along the direction of travel of said rack carrier part, a projection is provided in said moveable member for pushing a rear end of said sample rack and feeding the rack toward said rack carrier part, and a cam is provided in said moveable member at a position separated from said projection by a distance exceeding the length of each sample rack in a direction of travel of the sample racks, said cam is not engaged with a sample rack when said moveable member is moved in a direction for feeding said sample rack to said rack carrier part, and said cam is engaged with said sample rack when said moveable member returns said sample rack in an opposite direction.

16. An automatic chemical and biochemical analyzer using sample racks for conveying groups of individual samples, comprising:
an analysis unit having equipment for analyzing chemicals or biochemicals, said analysis unit including a separate sample rack conveyor;
a sample rack supply unit for supplying a plurality of sample racks to said analysis unit during operation, said sample rack supply unit including a separate sample rack conveyor;
a rack storage unit for receiving sample racks from said analysis unit during operation, said rack storage unit including a separate sample rack conveyor;
a first coupler for connecting said sample rack supply unit with said analysis unit during operation, and for aligning said separate conveyor or said sample supply unit with said separate conveyor of said analysis unit; and
a second coupler for connecting said analysis unit with said rack storage unit during operation, and for aligning said separate conveyor of said analysis unit with said separate conveyor of said analysis unit.

17. An analyzer according to claim 16, wherein said first and second couplers are defined by locating pins.

18. An analyzer according to claim 17, wherein said locating pins include a threaded male portion received within a threaded female portion.

19. An analyzer according to claim 17, wherein said first and second couplers are positioned adjacent and aligned with said conveyor.

20. An analyzer according to claim 17, wherein at least one of said first and second couplers is mounted on a support adjacent a guide plate and latch of one conveyor, which connects to a connecting pin of an adjacent conveyor to operationally couple conveyors of adjacent analysis units.

* * * * *